(12) United States Patent
Wang et al.

(10) Patent No.: US 7,576,155 B2
(45) Date of Patent: Aug. 18, 2009

(54) METHOD FOR CLAY EXFOLIATION, COMPOSITIONS THEREFORE, AND MODIFIED RUBBER CONTAINING SAME

(75) Inventors: Xiaorong Wang, Hudson, OH (US); Hiroyuki Fudemoto, Tokyo (JP); James E. Hall, Mogadore, OH (US); Shunji Araki, Kodaira (JP); Terrence Hogan, Akron, OH (US); Victor J. Foltz, Akron, OH (US); Pat Sadhukhan, Akron, OH (US); Georg G. A. Böhm, Akron, OH (US)

(73) Assignee: Bridgestone Corporation, Tokyo (JP)

(*) Notice: Subject to any disclaimer, the term of this patent is extended or adjusted under 35 U.S.C. 154(b) by 521 days.

(21) Appl. No.: 10/536,278

(22) PCT Filed: Dec. 18, 2003

(86) PCT No.: PCT/US03/40375

§ 371 (c)(1),
(2), (4) Date: Jan. 17, 2006

(87) PCT Pub. No.: WO2004/058874

PCT Pub. Date: Jul. 15, 2004

(65) Prior Publication Data

US 2006/0235128 A1   Oct. 19, 2006

Related U.S. Application Data

(60) Provisional application No. 60/434,481, filed on Dec. 18, 2002, provisional application No. 60/437,630, filed on Dec. 31, 2002.

(51) Int. Cl.
*C08K 9/04* (2006.01)

(52) U.S. Cl. .................. 524/445; 425/186; 425/447

(58) Field of Classification Search ............. 524/186, 524/445, 447; 508/145
See application file for complete search history.

(56) References Cited

U.S. PATENT DOCUMENTS

| | | | |
|---|---|---|---|
| 2,493,318 A | 1/1950 | Shonle et al. | |
| 2,531,396 A | 11/1950 | Carter et al. | |
| 3,598,884 A | 8/1971 | Wei | |
| 3,972,963 A | 8/1976 | Schwab et al. | |
| 4,233,409 A | 11/1980 | Bulkley | |
| 4,247,434 A | 1/1981 | Vanderhoff et al. | |
| 4,326,008 A | 4/1982 | Rembaum | |
| 4,338,206 A * | 7/1982 | Hammond et al. | 508/266 |
| 4,386,125 A | 5/1983 | Shiraki et al. | |
| 4,463,129 A | 7/1984 | Shinada et al. | |
| 4,543,403 A | 9/1985 | Isayama et al. | |
| 4,598,105 A | 7/1986 | Weber et al. | |
| 4,659,790 A | 4/1987 | Shimozato et al. | |
| 4,665,963 A | 5/1987 | Timar et al. | |
| 4,717,655 A | 1/1988 | Fulwyler | |
| 4,725,522 A | 2/1988 | Breton et al. | |
| 4,764,572 A | 8/1988 | Bean, Jr. | |
| 4,773,521 A | 9/1988 | Chen | |
| 4,774,189 A | 9/1988 | Schwartz | |
| 4,788,254 A | 11/1988 | Kawakubo et al. | |
| 4,829,130 A | 5/1989 | Licchelli et al. | |
| 4,829,135 A | 5/1989 | Gunesin et al. | |
| 4,837,274 A | 6/1989 | Kawakubo et al. | |
| 4,837,401 A | 6/1989 | Hirose et al. | |
| 4,861,131 A | 8/1989 | Bois et al. | |
| 4,870,144 A | 9/1989 | Noda et al. | |
| 4,871,814 A | 10/1989 | Gunesin et al. | |
| 4,904,730 A | 2/1990 | Moore et al. | |
| 4,904,732 A | 2/1990 | Iwahara et al. | |
| 4,906,695 A | 3/1990 | Blizzard et al. | |
| 4,920,160 A | 4/1990 | Chip et al. | |
| 4,942,209 A | 7/1990 | Gunesin | |
| 4,956,107 A * | 9/1990 | Gutierrez et al. | 508/194 |
| 5,034,018 A * | 7/1991 | Gutierrez et al. | 44/331 |
| 5,036,138 A | 7/1991 | Stamhuis et al. | |
| 5,066,729 A | 11/1991 | Stayer, Jr. et al. | |
| 5,073,498 A | 12/1991 | Schwartz et al. | |
| 5,075,377 A | 12/1991 | Kawakubo et al. | |
| 5,100,947 A | 3/1992 | Puydak et al. | |
| 5,112,507 A * | 5/1992 | Harrison | 508/192 |
| 5,120,379 A | 6/1992 | Noda et al. | |
| 5,130,377 A | 7/1992 | Trepka et al. | |
| 5,162,445 A * | 11/1992 | Powers et al. | 525/333.4 |
| 5,169,914 A | 12/1992 | Kaszas et al. | |
| 5,178,702 A | 1/1993 | Frerking, Jr. et al. | |
| 5,194,300 A | 3/1993 | Cheung | |
| 5,219,945 A | 6/1993 | Dicker et al. | |
| 5,227,419 A | 7/1993 | Moczygemba et al. | |
| 5,229,020 A * | 7/1993 | Gutierrez et al. | 508/194 |

(Continued)

FOREIGN PATENT DOCUMENTS

DE         3434983         4/1986

(Continued)

OTHER PUBLICATIONS

Bahadur, Pratap, "Block copolymers- Their microdomain formation (in solid state) and surfactant behaviour (in solution)", Current Science, vol. 80, No. 8, pp. 1002-1007, Apr. 25, 2001.

(Continued)

*Primary Examiner*—Katarzyna Wyrozebski (57) ABSTRACT

A polymer composition of low gas permeability. The composition includes an exfoliated organically-modified clay, butyl rubber, and a polymeric exfoliant. A method for producing the butyl composition by dry mixing the butyl rubber with the exfoliated clay is also provided.

21 Claims, 2 Drawing Sheets

U.S. PATENT DOCUMENTS

| | | | | |
|---|---|---|---|---|
| 5,237,015 | A | 8/1993 | Urban | |
| 5,238,466 | A * | 8/1993 | Gutierrez et al. | 44/331 |
| 5,241,008 | A | 8/1993 | Hall | |
| 5,247,021 | A | 9/1993 | Fujisawa et al. | |
| 5,256,736 | A | 10/1993 | Trepka et al. | |
| 5,262,502 | A | 11/1993 | Fujisawa et al. | |
| 5,290,873 | A | 3/1994 | Noda et al. | |
| 5,290,875 | A | 3/1994 | Moczygemba et al. | |
| 5,290,878 | A | 3/1994 | Yamamoto et al. | |
| 5,308,364 | A * | 5/1994 | Gutierrez et al. | 44/347 |
| 5,331,035 | A | 7/1994 | Hall | |
| 5,336,712 | A | 8/1994 | Austgen, Jr. et al. | |
| 5,385,684 | A * | 1/1995 | Gutierrez et al. | 508/189 |
| 5,395,891 | A | 3/1995 | Obrecht et al. | |
| 5,395,902 | A | 3/1995 | Hall | |
| 5,399,628 | A | 3/1995 | Moczygemba et al. | |
| 5,399,629 | A | 3/1995 | Coolbaugh et al. | |
| 5,405,903 | A | 4/1995 | Van Westrenen et al. | |
| 5,421,866 | A | 6/1995 | Stark-Kasley et al. | |
| 5,436,298 | A | 7/1995 | Moczygemba et al. | |
| 5,438,103 | A | 8/1995 | DePorter et al. | |
| 5,447,990 | A | 9/1995 | Noda et al. | |
| 5,462,994 | A | 10/1995 | Lo et al. | |
| 5,476,521 | A * | 12/1995 | Gutierrez et al. | 44/348 |
| 5,496,383 | A * | 3/1996 | Franz et al. | 44/432 |
| 5,514,734 | A | 5/1996 | Maxfield et al. | |
| 5,514,753 | A | 5/1996 | Ozawa et al. | |
| 5,521,309 | A | 5/1996 | Antkowiak et al. | |
| 5,525,639 | A | 6/1996 | Keneko et al. | |
| 5,527,870 | A | 6/1996 | Maeda et al. | |
| 5,567,845 | A * | 10/1996 | Franz et al. | 564/278 |
| 5,576,372 | A | 11/1996 | Kresge et al. | |
| 5,576,373 | A | 11/1996 | Kresge et al. | |
| 5,580,925 | A | 12/1996 | Iwahara et al. | |
| 5,587,423 | A | 12/1996 | Brandstetter et al. | |
| 5,594,072 | A | 1/1997 | Handlin, Jr. et al. | |
| 5,614,579 | A | 3/1997 | Roggeman et al. | |
| 5,627,252 | A | 5/1997 | De La Croi Habimana | |
| 5,633,326 | A * | 5/1997 | Patil et al. | 525/327.6 |
| 5,665,183 | A | 9/1997 | Kresge et al. | |
| 5,688,856 | A | 11/1997 | Austgen, Jr. et al. | |
| 5,707,439 | A | 1/1998 | Takekoshi et al. | |
| 5,728,791 | A | 3/1998 | Tamai et al. | |
| 5,733,975 | A | 3/1998 | Aoyama et al. | |
| 5,739,267 | A | 4/1998 | Fujisawa et al. | |
| 5,742,118 | A | 4/1998 | Endo et al. | |
| 5,763,551 | A | 6/1998 | Wunsch et al. | |
| 5,773,521 | A | 6/1998 | Hoxmeier et al. | |
| 5,777,037 | A | 7/1998 | Yamanaka et al. | |
| 5,807,629 | A | 9/1998 | Elspass et al. | |
| 5,811,501 | A | 9/1998 | Chiba et al. | |
| 5,834,563 | A | 11/1998 | Kimura et al. | |
| 5,847,054 | A | 12/1998 | McKee et al. | |
| 5,849,847 | A | 12/1998 | Quirk | |
| 5,855,972 | A | 1/1999 | Kaeding | |
| 5,883,173 | A | 3/1999 | Elspass et al. | |
| 5,891,947 | A | 4/1999 | Hall et al. | |
| 5,905,116 | A | 5/1999 | Wang et al. | |
| 5,910,530 | A | 6/1999 | Wang et al. | |
| 5,936,023 | A | 8/1999 | Kato et al. | |
| 5,955,537 | A | 9/1999 | Steininger et al. | |
| 5,986,010 | A | 11/1999 | Clites et al. | |
| 5,994,468 | A | 11/1999 | Wang et al. | |
| 6,011,116 | A | 1/2000 | Aoyama et al. | |
| 6,013,699 | A | 1/2000 | Freeman et al. | |
| 6,020,446 | A | 2/2000 | Okamoto et al. | |
| 6,025,416 | A | 2/2000 | Proebster et al. | |
| 6,025,445 | A | 2/2000 | Chiba et al. | |
| 6,034,164 | A | 3/2000 | Elspass et al. | |
| 6,060,549 | A * | 5/2000 | Li et al. | 524/445 |
| 6,060,559 | A | 5/2000 | Feng et al. | |
| 6,087,016 | A | 7/2000 | Feeney et al. | |
| 6,087,456 | A | 7/2000 | Sakaguchi et al. | |
| 6,106,953 | A | 8/2000 | Zimmermann et al. | |
| 6,117,932 | A | 9/2000 | Hasegawa et al. | |
| 6,121,379 | A | 9/2000 | Yamanaka et al. | |
| 6,127,488 | A | 10/2000 | Obrecht et al. | |
| 6,147,151 | A | 11/2000 | Fukumoto et al. | |
| 6,180,693 | B1 | 1/2001 | Tang et al. | |
| 6,191,217 | B1 | 2/2001 | Wang et al. | |
| 6,197,849 | B1 | 3/2001 | Zilg et al. | |
| 6,204,354 | B1 | 3/2001 | Wang et al. | |
| 6,225,394 | B1 | 5/2001 | Lan et al. | |
| 6,255,372 | B1 | 7/2001 | Lin et al. | |
| 6,268,451 | B1 | 7/2001 | Faust et al. | |
| 6,277,304 | B1 | 8/2001 | Wei et al. | |
| 6,348,546 | B2 | 2/2002 | Hiiro et al. | |
| 6,359,075 | B1 | 3/2002 | Wollum et al. | |
| 6,395,829 | B1 | 5/2002 | Miyamoto et al. | |
| 6,420,486 | B1 | 7/2002 | DePorter et al. | |
| 6,437,050 | B1 | 8/2002 | Krom et al. | |
| 6,441,090 | B1 | 8/2002 | Demirors et al. | |
| 6,472,460 | B1 | 10/2002 | Okamoto et al. | |
| 6,486,253 | B1 | 11/2002 | Gilmer et al. | |
| 6,489,378 | B1 | 12/2002 | Sosa et al. | |
| 6,524,595 | B1 | 2/2003 | Perrier et al. | |
| 6,573,330 | B1 | 6/2003 | Fujikake et al. | |
| 6,598,645 | B1 | 7/2003 | Larson | |
| 6,612,351 | B1 | 9/2003 | Zanzig | |
| 6,617,020 | B2 | 9/2003 | Zhou et al. | |
| 6,649,702 | B1 | 11/2003 | Rapoport et al. | |
| 6,689,469 | B2 | 2/2004 | Wang et al. | |
| 6,693,746 | B1 | 2/2004 | Nakamura et al. | |
| 6,706,804 | B2 | 3/2004 | Resendes | |
| 6,706,813 | B2 | 3/2004 | Chiba et al. | |
| 6,706,823 | B2 | 3/2004 | Wang et al. | |
| 6,727,311 | B2 | 4/2004 | Ajbani et al. | |
| 6,737,486 | B2 | 5/2004 | Wang | |
| 6,750,297 | B2 | 6/2004 | Yeu et al. | |
| 6,759,464 | B2 | 7/2004 | Ajbani et al. | |
| 6,777,500 | B2 | 8/2004 | Lean et al. | |
| 6,780,937 | B2 | 8/2004 | Castner | |
| 6,818,693 | B2 | 11/2004 | Heinrich et al. | |
| 6,835,781 | B2 | 12/2004 | Kondou et al. | |
| 6,849,680 | B2 | 2/2005 | Knudson, Jr. et al. | |
| 6,858,665 | B2 | 2/2005 | Larson | |
| 6,861,462 | B2 | 3/2005 | Parker et al. | |
| 6,872,785 | B2 | 3/2005 | Wang et al. | |
| 6,875,818 | B2 | 4/2005 | Wang | |
| 6,956,084 | B2 | 10/2005 | Wang et al. | |
| 7,019,063 | B2 | 3/2006 | Wada et al. | |
| 7,071,246 | B2 | 7/2006 | Xie et al. | |
| 7,112,369 | B2 | 9/2006 | Wang et al. | |
| 7,179,864 | B2 | 2/2007 | Wang | |
| 7,205,370 | B2 | 4/2007 | Wang et al. | |
| 7,241,829 | B2 | 7/2007 | Chung et al. | |
| 7,371,793 | B2 | 5/2008 | Gong et al. | |
| 7,388,033 | B2 * | 6/2008 | Nagy et al. | 516/67 |
| 2001/0053813 | A1 | 12/2001 | Konno et al. | |
| 2002/0007011 | A1 | 1/2002 | Konno et al. | |
| 2002/0045714 | A1 | 4/2002 | Tomalia et al. | |
| 2002/0095008 | A1 | 7/2002 | Heimrich et al. | |
| 2002/0144401 | A1 | 10/2002 | Nogueroles Vines et al. | |
| 2003/0004250 | A1 | 1/2003 | Ajbani et al. | |
| 2003/0032710 | A1 | 2/2003 | Larson | |
| 2003/0124353 | A1 | 7/2003 | Wang et al. | |
| 2003/0130401 | A1 | 7/2003 | Lin et al. | |
| 2003/0149185 | A1 | 8/2003 | Wang et al. | |
| 2003/0198810 | A1 | 10/2003 | Wang et al. | |
| 2003/0225190 | A1 | 12/2003 | Borbely et al. | |
| 2004/0059057 | A1 | 3/2004 | Swisher et al. | |
| 2004/0127603 | A1 | 7/2004 | Lean et al. | |
| 2004/0143064 | A1 | 7/2004 | Wang | |
| 2004/0147639 | A1 | 7/2004 | Tsou et al. | |

| | | | |
|---|---|---|---|
| 2004/0198917 | A1 | 10/2004 | Castner |
| 2004/0226643 | A1 | 11/2004 | Yagi et al. |
| 2004/0249045 | A1 | 12/2004 | Goodman et al. |
| 2005/0027057 | A1* | 2/2005 | Dias et al. .................. 524/445 |
| 2005/0027062 | A1 | 2/2005 | Waddell et al. |
| 2005/0090611 | A1* | 4/2005 | Huffer et al. ................. 524/800 |
| 2005/0098252 | A1 | 5/2005 | Muraoka et al. |
| 2005/0101743 | A1 | 5/2005 | Stacy et al. |
| 2005/0137288 | A1 | 6/2005 | Maruo et al. |
| 2005/0192408 | A1 | 9/2005 | Lin et al. |
| 2005/0197462 | A1 | 9/2005 | Wang et al. |
| 2005/0203248 | A1 | 9/2005 | Zheng et al. |
| 2005/0215693 | A1 | 9/2005 | Wang et al. |
| 2005/0222335 | A1 | 10/2005 | Jones et al. |
| 2005/0228074 | A1 | 10/2005 | Wang et al. |
| 2005/0277723 | A1* | 12/2005 | Gong et al. .................. 524/445 |
| 2005/0282956 | A1 | 12/2005 | Bohm et al. |
| 2006/0084722 | A1 | 4/2006 | Lin et al. |
| 2006/0100339 | A1* | 5/2006 | Gong et al. .................. 524/445 |
| 2006/0173115 | A1 | 8/2006 | Wang et al. |
| 2006/0173130 | A1 | 8/2006 | Wang et al. |
| 2007/0015853 | A1* | 1/2007 | Weng et al. .................. 523/333 |
| 2007/0129477 | A1* | 6/2007 | Weng et al. .................. 524/394 |
| 2007/0142550 | A1 | 6/2007 | Wang et al. |
| 2007/0142559 | A1 | 6/2007 | Wang et al. |
| 2007/0149649 | A1 | 6/2007 | Wang et al. |
| 2007/0161754 | A1 | 7/2007 | Bohm et al. |
| 2007/0185273 | A1 | 8/2007 | Hall et al. |
| 2007/0196653 | A1 | 8/2007 | Hall et al. |
| 2007/0238822 | A1* | 10/2007 | Wang et al. .................. 524/445 |
| 2008/0009579 | A1* | 1/2008 | Gong et al. .................. 524/445 |
| 2008/0081866 | A1* | 4/2008 | Gong et al. .................. 524/445 |

FOREIGN PATENT DOCUMENTS

| | | |
|---|---|---|
| DE | 4241538 | 6/1994 |
| EP | 143500 | 6/1985 |
| EP | 0 265 142 A2 | 4/1988 |
| EP | 0265145 | 4/1988 |
| EP | 0322905 | 7/1989 |
| EP | 0352042 | 1/1990 |
| EP | 0472344 | 2/1992 |
| EP | 0540942 | 5/1993 |
| EP | 0 590 491 A2 | 4/1994 |
| EP | 0742268 | 11/1996 |
| EP | 1031605 | 8/2000 |
| EP | 1 099 728 A1 | 5/2001 |
| EP | 1125927 | 8/2001 |
| EP | 1 134 251 A1 | 9/2001 |
| EP | 1273616 | 1/2003 |
| EP | 1321489 | 6/2003 |
| JP | 01279943 | 1/1989 |
| JP | 1955517 | 8/1989 |
| JP | 05132605 | 5/1993 |
| JP | 06248017 | 9/1994 |
| JP | 08-199062 | 8/1996 |
| JP | 3356001 | 10/2002 |
| JP | 2003-095640 | 4/2003 |
| WO | WO 91/04992 | 4/1991 |
| WO | 9704029 | 2/1997 |
| WO | 9853000 | 11/1998 |
| WO | WO 98/53000 | 11/1998 |
| WO | 9942518 | 8/1999 |
| WO | WO 01/87999 A2 | 11/2000 |
| WO | 0075226 | 12/2000 |
| WO | WO 02/31002 A1 | 4/2002 |
| WO | WO 02/081233 | 10/2002 |
| WO | WO 02/100936 A1 | 12/2002 |
| WO | 03032061 | 4/2003 |
| WO | WO 03/085040 | 10/2003 |
| WO | WO 2004/058874 A1 | 7/2004 |
| WO | WO 2004/065430 * | 8/2004 |
| WO | 2005/095506 | 10/2005 |

OTHER PUBLICATIONS

Guo, Andrew et al., "Star Polymers and Nanospheres from Cross-Linkable Diblock Copolymers", Macromolecules, vol. 29, pp. 2487-2493, Jan. 17, 1996.

Ishizu, Koji et al., "Core-Shell Type Polymer Microspheres Prepared from Block Copolymers", Journal of Polymer Science: Part C: Polymer Letters, vol. 26, pp. 281-286, 1988.

Ishizu, Koji, "Synthesis and Structural Ordering of Core-Shell Polymer Microspheres", Prog. Polym. Sci., vol. 23, pp. 1383-1408, 1998.

O'Reilly, Rachel K. et al., "Cross-linked block copolymer micelles: functional nanostructures of great potential and versatility", Chem. Soc. Rev., vol. 35, pp. 1068-1083, Oct. 2, 2006.

Oranli, Levent et al., "Hydrodynamic studies on micellar solutions of styrene-butadiene block copolymers in selective solvents", Can. J. Chem., vol. 63, pp. 2691-2696, 1985.

Pispas, S. et al., "Effect of Architecture on the Micellization Properties of Block Copolymers: $A_2B$ Miktoarm Stars vs AB Diblocks", Macromolecules, vol. 33, pp. 1741-1746, Feb. 17, 2000.

Riess, Gerard, "Micellization of block copolymers", Prog. Polym. Sci., vol. 28, pp. 1107-1170, Jan. 16, 2003.

Saito, Reiko et al., "Synthesis of microspheres with 'hairy-ball' structures from poly (styrene-b-2-vinyl pyridine) diblock copolymers", Polymer, vol. 33, No. 5, pp. 1073-1077, 1992.

Thurmond, K. Bruce et al., "Shell cross-linked polymer micelles: stabilized assemblies with great versatility and potential", Colloids and Surfaces B: Biointerfaces, vol. 16, pp. 45-54, 1999.

Wilson, D.J. et al., "Photochemical Stabilization of Block Copolymer Micelles", Eur. Polym. J., vol. 24, No. 7, pp. 617-621, 1988.

Ege, Seyhan, Organic Chemistry Structure and Reactivity, 3rd Edition, p. 959, 1994.

Star Polymers by Immobilizing Functional Block Copolymers, by Koji Ishizu, Tokyo Institute of Technology, Meguro-ku, Tokyo, Japan, Star and Hyperbranched Polymers, 1999, ISBN 0-8247-1986-7.

Formation of Worm-like Micelles from a Polystyrene-Polybutadiene-Polystyrene Block Copolymer in Ethyl Acetate, Canham et al., J.C.S. Faraday I, 1980, 76, 1857-1867.

Anomalous Behaviour of Solutions of Styrene-Butadiene Block Copolymers in Some Solvents, Tuzar et al., Makromol. Chem. 178, 22743-2746 (1977).

Association of Block Copolymers in Selective Solvents, 1 Measurements on Hydrogenated Poly(styrene-isoprene) in Decane and in trans-Decalin, Mandema et al., Makromol. Chem. 180, 1521-1538 (1979).

Light-Scattering Studies of a Polystyrene-Poly(methyl methacrylate) Two-Blcok Copolymer in Mixed Solvents, Utiyama et al. Macromolecules vol. 7, No. 4, Jul.-Aug. 1974.

Functionalized Core-Shell Polymers Prepared by Microemulsion Polymerization, E. Mendizabal et al., Dept. of Ingenieria Quimica, Unviv. De Guadalajara, MX, 477/ANTE 97/1733-1737.

Dendritic Macromolecules: Synthesis fo Starburst Dendrimers, Donald A. Tomalia et al., Macromolecules vol. 19, No. 9, 1986, contribution from Functional Polymers/Processes and the Analytical Laboratory, Dow Chemical, Midland, MI 48640, pp. 2466-2468.

Preparation and Characterization of Heterophase Blends of Polycaprolactam and Hydrogenated Polydienes, David F. Lawson et al., pp. 2331-2351, Central Research Labs., The Firestone Tire and Rubber Col, Akron, OH 44317, Journal of Applied Polymer Science, vol. 39, 1990 John Wiliey & Sons, Inc.

R.P. Quirk and S.C. Galvan, Macromolecules, 34, 1192-1197 (2001).

M. Moller, J.P. Spaz, A. Roescher, S. Mobmer, S.T. Selvan, H.A. Klok, Macromol. Symp. 117, 207-218 (1997).

T. Cosgrove, J.S. Phipps, R.M. Richardson, Macromolecules, 26, 4363-4367 (1993).

S. Mossmer, J.P. Spatz, M.Moller, T. Aberle, J. Schmidt, W. Burchard, Macromol. 33, 4791-4798 (2000).

Functionalized Core Shell Polymers Prepared by Microemulsion Polymerization,E. Mendizabel, J.E. Pugl, A. Aguiar, S. Gonzalez-Villegas, 477/Antec '97/1733-1737.

Ultrahydrophobic and Ultrayophobic Surfaces: Some Comments and Examples, Wei Chen et al., The ACS Journal of Surfaces and Colloids, May 11, 1999, vol. 15, No. 10, pp. 3395-3399, Polymer Science and Engineering Dept., Univ. of MA, Amherst, MA 01003.

Super-Repellent Composite Fluoropolymer Surfaces, S.R. Coulson, I. Woodward, J.P.S. Badyal, The Journal of Physical Chemistry B, vol. 104, No. 37, Sep. 21, 2000, pp. 8836-8840, Dept. of Chemistry, Science Laboratories, Durham University, Durham, DH1 3LE, England, U.K.

Akashi, Mitsuru et al., "Synthesis and Polymerization of A Styryl Terminated Oligovinylpyrrolidone Macromonomer", Die Angewandte Makromolekulare Chemie, 132, p. 81-89 (1985).

Alexandridis, Paschalis et al,."Amphiphilic Block Copolymers: Self-Assembly and Applications", Elsevier Science B.V., pp. 1-435 (2000).

Allgaier, Jurgen et al., "Synthesis and Micellar Properties of PS-PI Block Copolymers of Different Architecture", ACS Polym. Prepr. (Div Polym. Chem.), vol. 37, No. 2, pp. 670-671 (1996).

Antonietti, Markus et al., "Determination of the Micelle Architecture of Polystyrene/Poly(4-vinylpyridine) Block Copolymers in Dilute Solution", Macromolecules, 27, pp. 3276-3281 (1994).

Antonietti, Markus et al., "Novel Amphiphilic Block Copolymers by Polymer Reactions and Their Use for Solubilization of Metal Salts and Metal Colloids", Macromolecules, 29, pp. 3800-3806 (1996).

Batzilla, Thomas et al., "Formation of intra- and intermolecular crosslinks in the radical crosslinking of poly(4-vinylstyrene)", Makromol. Chem., Rapid Commun. 8, pp. 261-268 (1987).

Bauer, B.J. et al., "Synthesis and Dilute-Solution Behavior of Model Star-Branched Polymers", Rubber Chemistry and Technology, vol. 51, pp. 406-436 (1978).

Berger, G. et al., "Mutual Termination of Anionic and Cationic 'Living' Polymers", Polymer Letters, vol. 4, pp. 183-186 (1966).

Bradley, John S., "The Chemistry of Transition Metal Colloids", Clusters and Colloids: From Theory to Applications, Chapter 6, Weinheim, VCH, pp. 459-544 (1994).

Bronstein, Lyudmila M. et al., "Synthesis of Pd-, Pt-, and Rh-containing polymers derived from polystyrene-polybutadiene block copolymers; micellization of diblock copolymers due to complexation", Macromol. Chem. Phys., 199, pp. 1357-1363 (1998).

Calderara, Frederic et al., "Synthesis of chromophore-labelled polystyrene/poly(ethylene oxide) diblock copolymers", Makromol. Chem., 194, pp. 1411-1420 (1993).

Chen, Ming-Qing et al., "Graft Copolymers Having Hydrophobic Backbone and Hydrophilic Branches. XXIII. Particle Size Control of Poly(ethylene glycol)- Coated Polystyrene Nanoparticles Prepared by Macromonomer Method", Journal of Polymer Science: Part A: Polymer Chemistry, vol. 37, pp. 2155-2166 (1999).

Eisenberg, Adi, "Thermodynamics, Kinetics, and Mechanisms of the Formation of Multiple Block Copolymer Morphologies", Polymer Preprints, vol. 41, No. 2, pp. 1515-1516 (2000).

Erhardt, Rainer et al., Macromolecules, vol. 34, No. 4, pp. 1069-1075 (2001).

Eschwey, Helmut et al., "Preparation and Some Properties of Star-Shaped Polymers with more than Hundred Side Chains", Die, Makromolekulare Chemie 173, pp. 235-239 (1973).

Eschwey, Helmut et al, "Star polymers from styrene and divinylbenzene", Polymer, vol. 16, pp. 180-184 (Mar. 1975).

Fendler, Janos H., "Nanoparticles and Nanostructured Films: Preparation, Characterization and Applications", Wiley-VCH, pp. 1-468 (1998).

Garcia, Carlos B. et al., "Self-Assembly Approach toward Magnetic Silica-Type Nanoparticles of Different Shapes from Reverse Block Copolymer Mesophases", J. Am. Chem. Soc., vol. 125, pp. 13310-13311 (2003).

Hamley, Ian W., "The Physics of Block Copolymers", Oxford Science Publication: Oxford, Chapters 3 and 4, pp. 131-265, (1998).

Ishizu, Koji et al., "Synthesis of Star Polymer with Nucleus of Microgel", Polymer Journal, vol. 12, No. 6, pp. 399-404 (1980).

Ishizu, Koji, "Structural Ordering of Core Crosslinked Nanoparticles and Architecture of Polymeric Superstructures", ACS Polym. Prepr. (Div Polym Chem) vol. 40, No. 1, pp. 456-457 (1999).

Liu, Guojun et al., "Diblock Copolymer Nanofibers", Macromolecules, 29, pp. 5508-5510 (1996).

Ma, Qinggao et al., "Entirely Hydrophilic Shell Cross-Linked Knedel-Like (SCK) Nanoparticles", Polymer Preprints, vol. 41, No. 2, pp. 1571-1572 (2000).

Mayer, A.B.R. et al., "Transition metal nanoparticles protected by amphiphilic block copolymers as tailored catalyst systems", Colloid Polym. Sci., 275, pp. 333-340 (1997).

Mi, Yongli et al., "Glass transition of nano-sized single chain globules", Polymer 43, Elsevier Science Ltd., pp. 6701-6705 (2002).

Nace, Vaughn M., "Nonionic Surfactants: Polyoxyalkylene Block Copolymers", Surfactant Science Series, vol. 60, pp. 1-266 (1996).

Okay, Oguz et al., "Steric stabilization of reactive microgels from 1,4-divinylbenzene", Makromol. Chem., Rapid Commun., vol. 11, pp. 583-587 (1990).

Okay, Oguz et al., "Anionic Dispersion Polymerization of 1,4-Divinylbenzene", Macromolecules, 23, pp. 2623-2628 (1990).

Piirma, Irja, "Polymeric Surfactants", Surfactant Science Series, vol. 42, pp. 1-289 (1992).

Rager, Timo et al., "Micelle formation of poly(acrylic acid)- block-poly(methyl methacrylate) block copolymers in mixtures of water with organic solvents", Macromol. Chem. Phys., 200, No. 7, pp. 1672-1680 (1999).

Rein, David H. et al., "Kinetics of arm-first star polymers formation in a non-polar solvent", Marcomol. Chem. Phys., vol. 199, pp. 569-574 (1998).

Rempp, Paul et al., "Grafting and Branching of Polymers", Pure Appl. Chem., vol. 30, pp. 229-238 (1972).

Riess, Gerard et al., "Block Copolymers", Encyclopedia of Polymer Science and Engineering, vol. 2, pp. 324-434 (1985).

Saito, Reiko et al., "Synthesis of Microspheres with Microphase-Separated Shells", Journal of Polymer Science: Part A: Polymer Chemistry, vol. 38, pp. 2091-2097 (2000).

Serizawa, Takeshi et al., "Transmission Electron Microscopic Study of Cross-Sectional Morphologies of Core-Corona Polymeric Nanospheres", Marcomolecules, 33, pp. 1759-1764 (2000).

Stepanek, Miroslav et al. "Time-Dependent Behavior of Block Polyelectrolyte Micelles in Aqueous Media Studied by Potentiometric Titrations, QELS and Fluoroetry", Langmuir, Vo. 16, No. 6, pp. 2502-2507 (2000).

Thurmond II, K. Bruce et al., "Water-Soluble Knedel-like Structures: The Preparation of Shell-Cross-Linked Small Particles", J. Am. Chem. Soc., vol. 118, pp. 7239-7240 (1996).

Thurmond II, K. Bruce et al., "The Study of Shell Cross-Linked Knedels (SCK), Formation and Application", ACS Polym. Prepr. (Div Polym. Chem.), vol. 38, No. 1, pp. 62-63 (1997).

Tsitsilianis, Constantinos et al., Makromol. Chem. 191, pp. 2319-2328 (1990).

Tuzar, Zdenek et al., "Micelles of Block and Graft Copolymers in Solutions", Surface and Colloid Science, vol. 15, Chapter 1, pp. 1-83 (1993).

Vamvakaki, M. et al., "Synthesis of novel block and statistical methacrylate-based ionomers containing acidic, basic or betaine residues", Polymer, vol. 39, No. 11, pp. 2331-2337 (1998).

van der Maarel, J.R.C. et al., "Salt-Induced Contraction of Polyelectrolyte Diblock Copolymer Micelles", Langmuir, vol. 16, No. 19, pp. 7510-7519 (2000).

Wang, Xiaorong et al., "Chain conformation in two-dimensional dense state", Journal of Chemical Physics, vol. 121, No. 16, pp. 8158-8162 (Oct. 22, 2004).

Wang, Xiaorong et al., "Synthesis, Characterization, and Application of Novel Polymeric Nanoparticles", Macromolecules, 40, pp. 499-508 (2007).

Webber, Stephen E. et al., "Solvents and Self-Organization of Polymers", NATO ASI Series, Series E: Applied Sciences, vol. 327, pp. 1-509 (1996).

Wooley, Karen L., "From Dendrimers to Knedel-like Structures", Chem. Eur. J., 3, No. 9, pp. 1397-1399 (1997).

Wooley, Karen L., "Shell Crosslinked Polymer Assemblies: Nanoscale Constructs Inspired from Biological Systems", Journal of Polymer Science: Part A: Polymer Chemistry, vol. 38, pp. 1397-1407 (2000).

Worsfold, D.J., "Anionic Copolymerization of Styrene with p-Divinylbenzene", Macromolecules, vol. 3, No. 5, pp. 514-517 (Sep.-Oct. 1970).

Zheng, Lei et al., "Polystyrene Nanoparticles with Anionically Polymerized Polybutadiene Brushes", Macromolecules, 37, pp. 9954-9962 (2004).

Zilliox, Jean-Georges et al., "Preparation de Macromolecules a Structure en Etoile, par Copolymerisation Anionique", J. Polymer Sci.: Part C, No. 22, pp. 145-156 (1968).

Baranova, O.V. et al., "Effect of the Structure of Phase-Transfer Catalyst on the Rate of Alkaline Hydrolysis of N-Benzyloxycarbonylglycine 4-Nitrophenyl Ester in the System Chloroform-Borate Buffer", Russian Journal of Organic Chemistry, vol. 38, No. 3, pp. 378-384, 2002.

Wang, Yizhong et al., "Preparation and Characterization of Rubber-Clay Nanocomposites", Journal of Applied Polymer Science, vol. 78, pp. 1879-1883 (2000).

Webb, Paul B. et al., "Continuous Flow Hydroformylation of Alkenes in Supercritical Fluid-Ionic Liquid Biphasic Systems", J. Am. Chem. Soc., vol. 125, pp. 15577-15588, 2003.

Wilkes, John S. et al., "Dialkylimidazolium Chloroaluminate Melts: A New Class of Room-Temperature Ionic Liquids for Electrochemistry, Spectroscopy, and Synthesis", Inorg. Chem., vol. 21, pp. 1263-1264, 1982.

International Search Report with Written Opinion dated Dec. 27, 2007 from corresponding PCT Application No. PCT/US2007/071539 (11 pp.).

"Kink-Block and Gauche-Block Structures of Bimolecular Films" Gehard Lagaly, Chem. Int. Ed. Engl. vol. 15 (1976) No. 10, pp. 575-586.

"Linear Viscoelasticity of Disordered Polystyrene-Polyisoprene . . . Layered-silicate Nanocomposites" J. Ren, Dept. of Chem Eng. Univ. of Houston, Macromol. 2000, pp. 3739-3746.

"Rheology of End-Tethered Polymer Layered Silicate Nanocomposites," R. Krishnamoorti et al., Macromol. 1997, 30, 4097-4102.

"Rheology of Nanocomposites Based on Layered Silicates and Polyamide-12," B. Hoffman, et al., Colloid Polm. Sci. 278:629-636 (2000).

An article entitled "Quaternary Ammonium Compounds," Encyclopedia of Chemical Technology, 4th Ed. Vol. 20, 1996, Wiley &Sons, pp. 739-767.

Reverse Atom Transfer Radical Polymerization of Methyl Methacrylate in Room-Temperature Ionic Liqquids, H. Ma, X. Wan, X. Chen, Q-F. Zhou, J. Polym. Sci., A. Polym. Chem. 2003, 41, pp. 143-151.

"Dendrimers and Dendrons, Concept, Synthesis, Application", edited by Newkome G.R, Wiley-VCH, 2001, pp. 45, 191-310.

"Synthesis, Functionalization and Surface Treatment of Nanoparticles", edited by Baraton M-I, ASP (Am. Sci. Pub.), Stevenson Ranch, California, 2003, pp. 51-52, 174-208.

A Review of Nanocomposites 2000, J.N. Hay, S. J. Shaw.

Chemical Modification of Poly (styrene-co-maleic anhydride) with Primary N-Alkylamines by Reactive Extrusion, I Vermeesch et al., J. Applied Polym. Sci., vol. 53 pp. 1365-1373 (1994).

Dialkylimidazolium Chloroaluminate Melts: A New Class of Room-Temperature Ionic Liquids for Electrochemistry, Spectroscopy, and Synthesis, J.S. Wilkes, J.A. Levisky, B.A. Wilson, Inorg. Chem. 1982, 21, pp. 1263-1264.

EXAFS Investigations of the Mechanism of Facilitated Ion Transfer into a Room-Temperature Ionic Liquid. M. Jensen, J.A. Dzielawa, P. Rickert, M.L. Dietz, Jacs, 2002, 124, pp. 10664-10665.

Non-Debye Relaxations in Disordered Ionic Solids, W. Dieterich, P. Maass, Chem. Chys. 2002, 284, pp. 439-467.

Polymer Layered Silicate Nanocomposites, Giannelis E.P. Advanced Materials vol. 8, No. 1, Jan. 1, 1996 pp. 29-35.

Polymer-in-Ionic-Liquid Electrolytes C. Tiyapiboonchaiya, D.R. MacFarlane, J. Sun, M. Forsyth, Micromol. Chem. Phys., 2002, 203 pp. 1906-1911.

Polysulfobetaines and Corresponding Cationic Polymers. IV. Synthesis and Aqueous Solution Properties of Cationic Poly (MIQSDMAPM), Wen-Fu Lee et al., J. Appl. Pol. Sci. vol. 59, pp. 599-608 (1996).

Reaction of Primary Aliphatic Amines with Maleic Anhydride, Lester E. Coleman et al., J. Org. Chem., 24, 185 (1959), pp. 135-136.

Recent Advances in Flame Retardant Polymer Nanocomposites, Gilman, J.W. et al. pp. 273-283.

Simultaneous TA and MS Analysis of Alternating Styrene-Malei Anhydride and Styrene-Maleimide Copolymers, Thermochim. Acta, 277, 14 (1996).

Structure of molten 1,3-dimethylimidazolium chloride using neutron diffraction.C. Hardacre, J.D. Holbrey, S.E. J. McMath, D.T. Bowron, A.K. Soper, J. Chem. Physics, 2003, 118(1), pp. 273-278.

Synthesis and Photocrosslinking of Maleimide-Type Polymers, Woo-Sik Kim et al., Macromol. Rapid Commun., 17, 835 pp. 835-841 (1996).

Synthesis, Thermal Properties and Gas Pemeability of Poly (N-n-alkylmaleimide)s, A. Matsumoto et al., Polymer Journal vol. 23, No. 3, pp. 201-209 (1991).

Transformation of a Simple Plastic into a Superhydrophobic Surface, H. Yildirim Erbil et al., Science vol. 299, Feb. 28, 2003, pp. 1377-1380.

Ma, Yuhong et al., "Synthesis and Properties of the Ionomer Diblock Copolymer Poly(4-vinylbenzyl triethyl ammonium bromide)-b-Polyisobutene", Journal of Polymer Science: Part A: Chemistry, vol. 41, pp. 2755-2764 (2003).

Russell, G. , Feb. 22, 2006 International Preliminary Report on Patentability from PCT Patent Application No. PCT/US2005/010352 (7 pp.).

May 28, 2004 International Search Report from PCT Patent Application No. PCT/US03/40375 filed Dec. 18, 2003 (3 pp.).

Aug. 1, 2005 International Search Report from PCT Patent Application No. PCT/US2005/010352 filed Mar. 28, 2005 (3 pp.).

Dec. 27, 2007 International Search Report from PCT Patent Application No. PCT/US2007/071539 filed Jun. 19, 2007 (4 pp.).

* cited by examiner

METHOD FOR CLAY EXFOLIATION, COMPOSITIONS THEREFORE, AND MODIFIED RUBBER CONTAINING SAME

CROSS-REFERENCE TO RELATED APPLICATION

This application is a national stage application and claims the benefit of priority from PCT application PCT/US03/40375, published as WO 2004/058874, which was filed on Dec. 18, 2003, which in turn claims priority to both U.S. Provisional Application No. 60/434,481, filed on Dec. 18, 2002 and U.S. Provisional Application No. 60/437,630, filed on Dec. 31, 2002.

BACKGROUND OF THE INVENTION

The present invention relates to a rubber composition having low gas permeability. More particularly, the present invention relates to a clay filled butyl rubber composition having low gas permeability. Furthermore, the present invention relates to a process for the exfoliation of clay materials.

Butyl rubber is a synthetic elastomer typically comprised of a copolymer of isobutylene and isoprene. Butyl rubber was first produced with the advent of World War II and the associated limited supply of natural rubber.

Butyl rubber has a low degree of permeability to gases due to uniformity in the polyisobutylene portion of the butyl chains and the ease of packing provided by this uniformity. Butyl rubber can be 8-10 times more resistant to gas permeability than natural rubber and also has excellent resistance to heat, steam and water. The low degree of permeability to gases accounts for a frequent use of butyl rubber in inner tubes and tire inner liners. Similarly, butyl rubber is advantageously used in air cushions, pneumatic springs, air bellows, accumulator bags, and pharmaceutical closures. Furthermore, the thermal stability of butyl rubber makes it suitable for construction of tire-curing bladders, high temperature service hoses, and conveyor belts for handling hot-materials. Butyl rubber has also been used in damping mounts for engines and similar apparatus.

Notwithstanding its many desirable characteristics, in-chain unsaturation in butyl rubber, contributed by the presence of isoprene monomer units in the backbone, can be attacked by atmospheric ozone. These attacks may, over time, lead to oxidative degradation, which may subsequently lead to chain cleavage. This potential breakdown of the rubber could result in lower damping properties. One way to limit the impact of atmospheric gases on the butyl rubber structure is to further lower the gas permeability of the rubber composition.

It is known that the addition of exfoliated clays to certain types of rubber compositions may be an effective way to lower gas permeability. To lower gas permeability in rubber, the added clay must be of a small size, a condition traditionally achieved by exfoliation. Typical clays, prior to exfoliation, have a layered structure with a gap of about 0.1 nm between each layer and positively charged ions on the surface of each layer. The positively charged ions are attached by an ionic interaction with the negative surface of the clay layers, and create a net neutral charge between clay layers.

Traditional exfoliation is generally conducted as follows. Clay is first swelled by placing it in water. Swelling takes place because the positively charged ions become solubilized in the water, leaving adjacent negatively charged clay layers. The adjacent clay layers are repulsed by their similar negative charges, resulting in gaps of up to about 3 nm between the layers. An organic salt, such as cetyltrimethylammonium bromide or benzalkonium chloride is then added to the swollen clay to form an organo-clay. The organic salt is attracted to the negatively charged surface of the clay, keeping the swelling state stable and gaps of about 5-10 nm between the layers. This organo-clay is then dried and subsequently placed in an organic solvent, such as toluene. A polymer such as polypropylene or nylon is then added to further separate the layers of the clay. Moreover, the polymer is attracted to the organic salt and therefore penetrates between clay layers. The large molecule size of the polymer serves to counteract any remaining Van der Waals interactions between the layers and the clay becomes fully exfoliated, i.e. separated into discrete layers.

Previous attempts to incorporate exfoliated clay in butyl rubber have proven largely unsuccessful due to the poor interaction of butyl rubber with the organic salts used to make the organo-clay. Therefore, it would be desirable to develop an improved method of dispersing an exfoliated clay in butyl rubber to lower gas permeability.

SUMMARY OF THE INVENTION

The present invention is directed to a modified clay product which can be incorporated into butyl rubber.

In accordance with the above, a first aspect of the invention is to provide a polymeric exfoliant that is an exfoliant for clay.

A further aspect of the invention is to provide a method for exfoliating clay by using the polymeric exfoliant that will exfoliate the clay.

Another aspect of the invention relates to a process for producing a randomly $NR_2$-functionalized poly(isobutylene) by co-polymerizing isobutylene with a vinylbenzylamine compound.

A further aspect of the invention relates to the synthesis of poly(isobutylene-co-N,N-dimethylvinylbenzylamine) by copolymerizing isobutylene and N,N dimethylvinylbenzylamine.

A further aspect of the invention relates to making polyisobutylene quaternary salt (PIBQS), polyisobutylene with multiple quaternary salts ($PIB_2QS_2$), or polyisobutylene amine salt (PIBAS) by reacting polyisobutylene succinic anhydride (PIBSA) with a tertiary amine and a quaternizing agent or HCl.

A further aspect of the invention is to provide a method for lowering the gas permeability of butyl rubber by incorporating an exfoliated organo-modified clay into the butyl rubber. The polymeric exfoliant, such as PIBQS, $PIB_2QS_2$, PIBAS, poly(isobutylene-co-N,N-dimethylvinylbenzylamine) or modified butyl rubber can be reacted with clay and used alone without using an organo-modified clay, or advantageously used in combination with a low molecular weight surfactant used to form an organo-modified clay.

A further aspect of the invention is to provide a butyl rubber composition that has been modified with an exfoliated clay thereby imparting low gas permeability properties to the butyl rubber.

Another aspect of the invention is to provide a butyl rubber composition having low gas permeability wherein an exfoliant selected from poly(isobutylene-co-N,N-dimethylvinylbenzylamine), polyisobutylene quaternary ammonium salt (PIBQS), polyisobutylene amine salt (PIBAS), polyisobutylene with multiple quaternary salts, ($PIB_2QS_2$)r modified butyl rubber is admixed with an organo-modified clay and butyl rubber.

A further aspect of the invention is to provide a method for making an organo-modified clay product which can be exfoliated into butyl rubber by dry mixing.

These and other aspects and advantages of the present invention will become apparent upon reading the detailed description below.

BRIEF DESCRIPTION OF THE DRAWINGS

The invention may take form in various components and arrangements of components, and in various steps and arrangements of steps. The drawings, in which like reference numerals denote like components throughout the several views, are only for purposes of illustrating preferred embodiments and are not to be construed as limiting the invention.

DETAILED DESCRIPTION OF ILLUSTRATIVE EMBODIMENTS

The present invention provides a butyl rubber composition with low gas permeability. The low gas permeability of the composition is achieved by dispersing an exfoliated clay in a butyl rubber composition. The inclusion of an exfoliated clay in the butyl rubber helps to reduce the gas permeability, thereby increasing and prolonging the damping properties of the butyl rubber composition.

A variety of clays may be implemented in the present invention, provided the clay is capable of being exfoliated. Exemplary clays include, but are not limited to, pyrophyllite, smectites, illites, glauconites, vermiculites, polygorskines, sepiolites, allophanes, imogolites, synthetic mica, and mixtures thereof. Preferred clays are smectites, and the most preferred smectites are montmorillonite (Bentonite), beidellite, nontronite, hectorite, saponite, sauconite, and mixtures thereof.

The initial step in the clay exfoliation may include treating the clay with one or more low molecular weight organic surfactants to obtain an organically modified clay. More particularly, an ionic organic surfactant having a molecular weight of less than about 2000, preferably less than about 500 is used to form an organo-modified clay.

Exemplary materials include organic salts which may have the general structure:

wherein X is a halide and $R^1$, $R^2$, $R^3$, and $R^4$ are selected from H and $C_1$-$C_{30}$ alkyl chains, which may be linear or branched, further wherein the alkyl chain may optionally contain an aromatic moiety. At least one of $R^1$-$R^4$ should be a $C_4$-$C_{30}$ alkyl chain as described previously.

Preferred ionic organic surfactant materials include organic ammonium salts, such as dimethyldioctadecyl ammonium. Other organic salts include, but are not limited to, cetyltrimethylammonium bromide, and benzalkonium chloride, and mixtures thereof. Alternatively, a polar polymeric material such as a polyether may be employed.

An exfoliation polymer can then be added to the solution containing the organically modified clay. The exfoliation polymer according to the present invention is one which will exfoliate into organically modified clay and preferably compatabilize the clay with butyl rubber; The exfoliated clay, when combined with the butyl rubber, provides a butyl rubber which has low gas permeability.

In accordance with the invention, polymeric compounds have been developed which, when incorporated into a clay product, possess the desired property of being able to exfoliate the clay into butyl rubber to lower the gas permeability of the butyl rubber.

According to one embodiment of the invention, the exfoliation polymer is a modified butyl rubber. Preferred butyl rubber compositions include (i) alkene monomers such as ethylene, propylene, butylenes, isobutylene, pentene, hexene, heptene, etc., as well as any di- or tri-alkene, or mixtures thereof, and (ii) multiolefin monomers, such as isoprene, p-methylstyrene or mixtures thereof. The butyl rubber is typically composed of approximately 70-99.5 mol percent of alkene units and approximately 30-0.5 mol percent of multiolefin units, and preferably approximately 90-99.5 mol percent of alkene units and 10-0.5 mol percent multiolefin units.

The term "multiolefin", as used herein, includes olefins of 4-16 carbon atoms, such as butadiene, cyclopentadiene, piperylene, isoprene, and 1,3-dimethylbutadiene, isoprene; 2,3-dimethyl-butadiene-1,3; 1,2-dimethyl-butadiene-1,3 (3-methyl pentadiene-1,3); 1,3-dimethyl butadiene-1,3; 1-ethyl butadiene-1,3 (hexadiene-1,3); 1,4-dimethyl butadiene-1,3 (hexadiene-2,4); and methylstyrene.

These butyl rubbers can be prepared according to any polymerization process known in the art but are also "modified" by bromination, wherein a reactive benzylic-bromine functionality is formed selectively on the vinyl aromatic monomers. Particularly preferred modified butyl rubbers include poly(ethylene-co-propylene-co-bromo-p-methylstyrene), available as Exxpro™.

One further exemplary compound which has the desired properties of exfoliating clay into butyl rubber to lower the gas permeability of the butyl rubber is a randomly $NR_2$-functionalized poly(isobutylene). A process for preparing the randomly $NR_2$-functionalized poly(isobutylene) involves copolymerizing isobutylene and a compound having the formula (I):

where $R^1$ is a bond or is an alkylene group selected from $C_1$-$C_{18}$ linear or branched alkylene, $C_3$-$C_{20}$ cycloalkylene and $C_6$-$C_{24}$ arylene groups where $R^1$ may contain ether or tertiary amine groups. The $R^2$ and $R^3$ groups are independently selected from $C_1$-$C_{18}$ linear or branched alkyl, $C_3$-$C_{20}$ cycloalkyl and $C_6$-$C_{24}$ aromatic where the $R^2$ and $R^3$ groups may contain ether or tertiary amine groups.

The substituents on the vinyl aromatic group may be attached in any of the meta, ortho, or para positions. In these styryl derivatives, the para position is preferred. The $R^1$ group forms a linkage between the vinyl aromatic hydrocarbon and the amine group, however if $R_1$ is an ether, the part of the $R_1$ group attached to amine should be alkylene. Alternatively, the amine may be attached directly to the vinyl aromatic hydrocarbon. Of course, the invention also includes napthalene and other vinyl aromatic monomers wherein the $R^1NR^2R^3$ substituent can be attached at any ring position. Typically the compound of formula (1) is an N,N-dialkylaminoalkylenyl substituted styrene.

The co-polymerization of the isobutylene and the compound of formula (I) takes place in a solvent system in the presence of a Lewis acid or Bronsted acid. The polymerization reaction can be initiated by a carbenium ion. Typical methods for generating suitable carbenium ions are by reaction of alkyl halides with Lewis acids or reaction of Bronsted acids with an alkene. In the Lewis acid system, the polymerization is initiated by the presence of an alkyl halide and a Lewis acid, the former may be referred to herein as an initiator and the latter as a co-initiator. Accordingly, the Lewis acid and alkyl halide may be first combined and added to the vinyl aromatic and tertiary alkene monomers and or added thereto separately in any order. The preferred method is to add the alkyl halide to the monomers and then add the Lewis acid. Multifunctional initiators may be synthesized using polyhalogenated species and a Lewis acid. Preferred initiator systems include Lewis acids, such as $TiCl_4$, $BCl_3$, $AlCl_3$, $Et_2AlCl$, $EtAlCl_2$, and mixtures thereof, and an alkyl halide from the list α, α, α', α' tetramethyl-1,4-benzene dimethyl chloride, t-butyl chloride, t-butyl bromide, 2-chloro-2-phenylpropane, 2-bromo-2-phenylpropane, 2-chloro-2-methylpentane, 2-bromo-2-methylpentane, 2-chloro-2-methylbutane, 2-bromo-2-methylbutane, 1,3-(2-chloro-2-propyl)-5-t-butyl benzene and 1,3-(2-bromo-2-propyl)-5-t-butyl benzene, and mixtures thereof. A preferred initiator system is α, α, α', α' tetramethyl-1,4-benzene dimethyl chloride and titanium tetrachloride.

It is known that Lewis acids, particularly $TiCl_4$, will react with nitrogen containing species. Accordingly, since a tertiary amine group is a required constituent of the copolymerized vinyl aromatic monomers, one skilled in the art may expect this to deactivate Lewis acid catalysts. Surprisingly, this does not occur in the present polymerization. As a result, $TiCl_4$ co-initiation of the copolymerization of tertiary alkene monomers and tertiary amine substituted vinyl aromatic hydrocarbons provides an efficient, one-step polymerization process.

The polymerization is preferably carried out at low temperatures, such as below about 0° C., more preferably below about −20° C., and most preferably below about −50° C., under an inert atmosphere, such as $N_2$ or Ar. The initiator is added to a charge of substituted vinyl aromatic hydrocarbon monomer and tertiary alkene monomer in a polymerization vessel and living polymerization is initiated by addition of the co-initiator. The alkyl halide is added in an amount of about 0.001 to 0.1 mol per 100 grams monomer, more preferably between about 0.004 and 0.1 mol per 100 grams monomer, most preferably between about 0.004 and 0.02 mol per 100 grams monomer. The polymerization is allowed to continue until substantially 100% of monomer conversion is completed. The polymerization can be terminated by the addition of a terminator, such as an alcohol, although other terminators known in the art would also be suitable. The resulting polymers are tertiary amine modified polyisobutylene. The polymer compositions thus formed may be telechelic and/or may include random polymerization of the tertiary alkene and vinyl aromatic hydrocarbon monomer units.

The polymer preferably has a $M_n$ range of about 1000 to about 100,000, more preferably between about 1000 and 25,000 as measured by gel permeation chromatography (GPC) using universal calibration and the following Mark-Houwink constants for polyisobutylene: K=0.000085, α=0.75. Tertiary alkene monomer contributed units preferably comprise between about 46.6 and 99.5 wt % of the total polymer composition, more preferably between about 89.3 and 97.9 wt % of the total polymer composition, while the substituted vinyl aromatic contributed units comprise between about 54.4 and 0.5 wt % of the total polymer composition, more preferably between about 10.7 and 2.1 wt %.

In a more specific embodiment, a process for synthesizing a randomly $NR_2$-functionalized poly(isobutylene) by cationic polymerization comprises the steps of:
a) mixing isobutylene in a solvent system;
b) cooling the isobutylene/solvent mixture;
c) adding N,N-dimethylvinylbenzylamine to the mixture along with an initiator and modifiers;
d) initiating a polymerization reaction by adding $TiCl_4$;
e) terminating the polymerization with MeOH; and
f) evaporating any remaining solvents;

wherein the resulting product of poly(isobutylene-co-N,N-dimethylvinylbenzylamine) is yielded.

The solvent system may comprise solvents, such as hydrocarbon solvents, including hexane and heptane, aromatic solvents including toluene and xylene, chlorinated solvents including methylchloride, methylene chloride, chloroform, and mixtures of these. In one embodiment, the solvent system comprises hexane and methyl chloride.

In an alternative embodiment, the exfoliation polymer comprises surfactant includes, for example, PIBQS, PIBAS, $PIB_2QS_2$, and poly(isobutylene-co-N,N-dimethylvinylbenzylamine). The exfoliation polymeric surfactant can be dissolved in a solvent such as, for example, THF, diethyl ether, toluene, isopropanol, acetone, methyl ethyl ketone (MEK), and any other solvent(s) that will dissolve the exfoliation polymer and would not interfere with the intercalation ability of the polymer. Alcohol can also be added to the polymer THF mixture.

A process for preparing PIBQS, $PIB_2QS_2$ and PIBAS involves reacting polyisobutylene succinic anhydride (PIBSA) with a tertiary amine to produce polyisobutylene succinimide which is then reacted with HCl to form the PIBAS or an alkylating agent to form PIBQS/$PIB_2QS_2$. Suitable alkylating agents to form quat salts include, but are not limited to, methyl chloride, benzyl chloride, dimethyl sulfate, diethylsulfate, and α,α'-dibromo-xylene. A review of quaternary ammonium compounds can be found in the *Encyclopedia of Chemical Technology*, 4th edition, (1996), John Wiley and Sons.

In particular, the process for preparing the PIBQS comprises:

a) mixing polyisobutylene succinic anhydride (PIBSA) with a multi-amine compound selected from, for example, 3-(dimethylamino)propylamine, tetraethylene pentamine, 3,3'-diamino-N-methyl dipropylamine, 1-(2-aminoethyl)piperazine, 4-amino-1-benzylpiperidine, dimethylaminovinylbenzylamine, polyethyleneimine, 3-aminopyrrolidine, 3-(dimethylamino)pyrrolidine and N,N'-Bis(3-aminopropyl)ethylene diamine;

b) heating the mixture to about 150° C.;

c) maintaining the heated mixture at about 150° C. for about five minutes;

d) allowing the mixture to cool;

e) adding HCl and water to the cooled mixture of step d);

wherein PIBAS is thereby formed.

By first dissolving the polymeric surfactant into a solvent, i.e., the polymeric surfactant dissolved into THF diethyl ether, MEK or other solvents which would dissolve the polymeric surfactant and would not interfere with the intercalation ability of the polymer, and then subsequently adding this to the swelled clay, the ion exchange reaction necessary for the polymer surfactant to diffuse into the swelled clay sheets becomes possible. Using this alternative procedure, it is possible for the polymer surfactant to diffuse into and intercalate the clay.

The organo-modified clay provided in accordance with the alternative embodiment can be advantageously exfoliated into butyl rubber by a dry mixing method under mild mixing conditions compared to conventional exfoliation processes. Such mild mixing conditions are, for example, similar to those normally used in butyl rubber mixing. The mixing conditions may be accomplished, for example, by using any integral mixing devices such as a Bradender mixer, a twin-screw extruder or a kneader, at a mixing rate of from about 1 to about 500 rpm and a temperature of about 25° C. to about 300° C. for a period of up to about ten minutes. Typical butyl rubber mixing conditions are, for example, using a Brabender mixer at about 30 to about 120 rpm, at about 70° C. to about 175° C. for about two to about ten minutes. In one embodiment the butyl rubber mixing conditions are for example, mixing at about 60 rpm at a temperature of about 70° C. for about three minutes. Preferably, the clay is at least about 85% exfoliated, more preferably at least about 90% exfoliated. The exfoliated clay preferably has a plate size between about 0.1 and about 100 μm.

The organically-modified swollen clay, organic solvent, and polymeric surfactant are preferably combined to yield a solution containing between about 40 and about 95 wt. % solvent, more preferably between about 70 and about 90 wt. %; between about 5 and about 25 wt. % polymer, more preferably between about 8 and about 20 wt. %; and between about 0.01 and about 8 wt. % clay, more preferably between about 0.25 and about 6 wt. %. Preferably, the clay/organic solvent/polymer solution will include at least about 5% clay particles.

Gas permeability has been improved by using the clay treated with the combination of the exfoliation polymer and the low molecular weight surfactant. However, it can be difficult for the exfoliation polymer to be dissolved into aqueous solution. Alternatively, it can be difficult for the low molecular weight surfactant to be dissolved into organic solvent. Furthermore, water is advantageously used in clay swelling and for an ion exchange reaction. Accordingly, a preferred method for carrying out the invention includes first dissolving the exfoliation polymer into THF and separately forming a mixture of clay and low molecular weight surfactant. The exfoliation polymer solution is then added to the mixture of the clay and the low molecular weight surfactant. After that, alcohol and water are added to the solution. This procedure provides the exfoliation polymer and the low molecular weight surfactant with improved mechanisms to diffuse into and intercalate the clay. As the result, it is believed that the exfoliation polymer and the low molecular weight surfactant exchanges the sodium ion of the clay.

After the exfoliation step has been completed, the clay/organic solvent/polymer solution (now an exfoliated clay) can be dried to yield an exfoliated clay/polymer composition and added to a butyl rubber composition. It is also contemplated that the clay/polymer composition be separated from the organic solvent, e.g., by filtration or evaporation. Of course, it is also envisioned that the exfoliated clay can be added in the form of the solution comprised of a polymeric surfactant organically modified clay and solvent. As used herein, the butyl rubber composition is intended to include isobutylene, halobutyl rubber, and copolymers of isobutylene and one or more additional monomers, such as isoprene, styrene, butadiene, and mixtures thereof.

The exfoliated clay/polymer composition is typically added to the butyl rubber at elevated temperatures, such as between about 50° C. to about 175° C., preferably between about 70° C. and about 150° C., more preferably between about 80° C. and about 140° C. The addition can be carried out as a dry mixing process in any conventional mixer, such a Brabender mixer, which is preferably purged with an inert gas such as $N_2$ prior to charging the components. The addition of the clay/polymer composition may be also carried out at a pressure from slightly above vacuum to about 2100 kPa, under substantially dry conditions. Of course, the butyl rubber can be added according to any method known by the skilled artisan.

In any event, it is preferred that between about 1 and about 99% by weight clay/polymer composition is incorporated in the butyl rubber composition. More preferably, between about 3 and about 70%. Most preferably, it is desirable that a suitable amount of clay/polymer composition be dispersed in the butyl rubber composition to achieve an air permeability less than about 100 mL/m$^2$ day, more preferably less than about 80 mL/m$^2$ day. Because butyl rubber compositions can vary with respect to starting air permeability, the addition of the clay/polymer composition preferably achieves an at least about 20% reduction in air permeability, more preferably, at least about 50%.

It is frequently desirable to include other additives known in the art to the compositions of the present invention. Suitable additives include stabilizers, antioxidants, conventional fillers, processing aids, accelerators, extenders, curing agents, reinforcing agents, reinforcing resins, pigments, fragrances, and the like. Other additives known in the art are also contemplated for use in the present invention. Specific examples of useful antioxidants and stabilizers include 2-(2'-hydroxy-5'-methylphenyl)benzotriazole, nickel di-butyl-dithiocarbamate, tris(nonylphenyl)phosphite, 2,6-di-t-butyl-4-methylphenol, and the like. Exemplary conventional fillers and pigments include silica, carbon black, titanium dioxide, iron oxide, and the like. Suitable reinforcing materials are inorganic or organic products of high molecular weight. Examples include glass fibers, asbestos, boron fibers, carbon and graphite fibers, whiskers, quartz and silica fibers, ceramic fibers, metal fibers, natural organic fibers, and synthetic organic fibers. These compounding ingredients are incorporated in suitable amounts depending upon the contemplated use of the product, preferably in the range of about 1-350 parts of additives or compounding ingredients per 100 parts of the butyl rubber composition.

The butyl rubber composition of the present invention is useful in the formation of inner liners for automobile tires and in applications requiring good damping characteristics, such as engine mounts. Other uses for the butyl rubber compositions of the invention include use in air cushions, pneumatic springs, air bellows, accumulator bags, tire-curing bladders, high temperature service hoses, and conveyor belts for handling hot materials.

In the following, the present invention will be described in more detail with reference to non-limiting examples. The following examples and tables are presented for purposes of illustration only and are not to be construed in a limiting sense.

EXAMPLES

Synthesis of Initiator 400 mL of $CH_2Cl_2$ and 41.68 g (0.215 mol) $\alpha,\alpha,\alpha',\alpha'$-tetramethyl-1,4-benzene dimethanol (99%, Aldrich) were added to a nitrogen purged, 3-necked 1000 mL round bottom flask equipped with a reflux condensor with stirring. To this solution was slowly added 31.3 mL (0.215 mol) of thionyl chloride (99+%, Aldrich) over 15 minutes. After 12 hours, the solution was rotary evaporated yielding white crystals of $\alpha,\alpha,\alpha',\alpha'$-tetramethyl-1,4-benzene dimethylchloride. The product was recrystallized twice from hexane and stored at −20° C. until used. Directly prior to use, the crystals were recrystallized once more from hexane to obtain $\alpha,\alpha,\alpha',\alpha'$-tetramethyl-1,4-benzene dimethylchloride: mp=69-70° C., $^1$H-NMR($CDCl_3$): 7.56 ppm, 4H, s; 1.99 ppm, 12H, s.

Example 1

Synthesis of Poly(isobutylene-co-N,N-dimethylvinylbenzylamine)

To a 1 L $N_2$ purged bottle was added 173.2 g of 23 wt. % isobutylene in hexane and 272.6 g of methyl chloride with stirring. The bottle was cooled to −78° C. and 1.5 mL dimethylacetamide (Aldrich), 0.8 mL di-t-butylpyridine (Aldrich), 1.98 g of $\alpha,\alpha,\alpha',\alpha'$-tetramethyl-1,4-benzene dimethylchloride (prepared according to the synthesis set forth above) and 1.38 g of N,N-dimethylvinylbenzylamine (Aldrich) were added. Upon addition of 4 mL of $TiCl_4$ (Aldrich) the polymerization was initiated and the temperature rose to −60.7° C. After 43 minutes, an additional 2 mL of $TiCl_4$ was added. After 90 minutes, the reaction was terminated with 20 mL methanol. The methyl chloride was evaporated and the resulting hexane solution extracted with 300 mL methanol. Evaporation of the solvent yielded poly(isobutylene-co-N,N-dimethylvinylbenzylamine) with the following properties: $Mn=9.4\times10^3$ g/mol, $M_w=1.34\times10^4$ g/mol. Integraion of the $N-(CH_3)_2$ peaks in the $^1$H-NMR spectrum and comparison to the polyisobutylene methyl group revealed 1.67 N,N-dimethylvinylbenzylamine incorporated per chain.

Example 2

Organo-Montmorillonite

The layered silicate was a montmorillonite (a natural Bentonite clay from Southern Clay Products, Gonzales, Tex.) with a charge exchange capacity (CEC) of about 98 mequiv/100 g. The clay was organically modified with benzalkonium chloride (Aldrich, Milwaukee, Wis.) through a cation exchange reaction. In this reaction, 200 mL of a benzalkonium chloride/water solution (30 wt. %) was used to treat 50 g of the clay. The reaction was performed in a sealed flask and the reactants were shaken for 20 hrs at 23° C. The mixture was then filtered through a filter paper. Thereafter, the clay was dispersed in another 200 mL of the benzalkonium choride/water solution. The process was repeated three times. Finally, excess benzalkonium chloride was removed using isopropanol to wash the product. After vacuum drying, the modified montmorillonite contained about 45% organo-matter (i.e., benzalkonium), as measured by thermo-gravity analysis (TGA). TGA was carried out on equipment manufactured by TA Instruments and Perkin Elmer, among others.

Examples 3-5

Clay Particle Exfoliation

Figure 1:
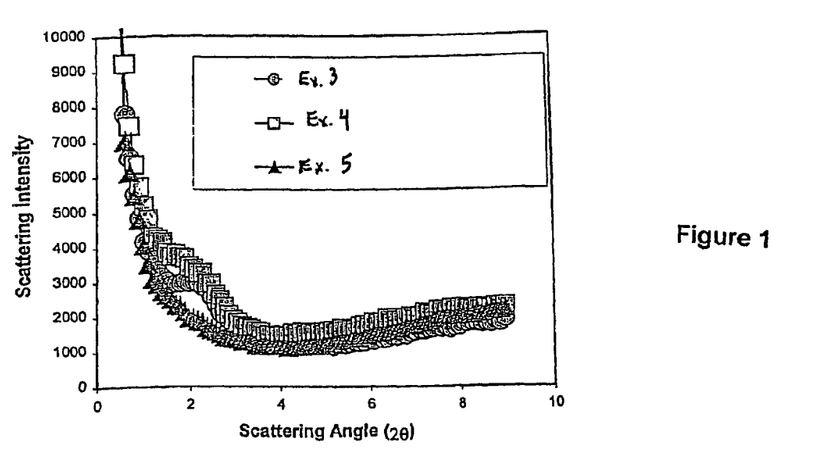
FIG. 1 shows small angle x-ray scattering (SAXS) of poly (isobutylene-co-N,N-dimethylvinylbenzylamine) exfoliated clay in butyl rubber.

The required amounts (from Table 1 below) of toluene, butyl rubber (MH-11), treated silicate (example 2), and a 10 wt. % solution of poly(isobutylene-co-N,N-dimethylvinylbenzylamine) (Example 1) in toluene were charged into a 950 mL bottle. The bottle was then placed on a mechanical shaker for 24 hours, and the polymer and treated silicate were dissolved in toluene. Excess surfactant was then extracted with EtOH and the resulting material was then drum dried. Small angle x-ray scattering (SAXS) shows that addition of poly(isobutylene-co-N,N-dimethylvinylbenzylamine) improves the exfoliation of the clay into the butyl rubber (FIG. 1). Particularly, in example 5, where no montmorillonite lamellar peak was observed, indicating that the clay is completely exfoliated.

TABLE 1

|  | Example 3 | Example 4 | Example 5 |
|---|---|---|---|
| Toluene ml | 300 | 255 ml | 180 ml |
| MH-11 (g) | 40 | 40 | 40 |
| Treated silicate (g) | 4 | 4 | 4 |
| 2562-71-1* | 0 | 45 ml | 120 ml |

*2562-71-1 is a 10 wt. % solution of poly(isobutylene-co-N,N-dimethylvinylbenzylamine) in toluene The following table shows the effects of the poly(isobutylene-co-N,N-dimethylvinylbenzylamine) treated clay on gas permeability of butyl rubber.

TABLE 2

| Pure Butyl Rubber (GPI-gas permeability index)** | Butyl Rubber + organo-clay + 2562-71-1 (GPI-gas permeability index) |
|---|---|
| 1 | 0.294 |
| 1 | 0.384 |
| 1 | 0.304 |

TABLE 2-continued

| | Pure Butyl Rubber (GPI-gas permeability index)** | Butyl Rubber + organo-clay + 2562-71-1 (GPI-gas permeability index) |
|---|---|---|
| | 1 | 0.457 |
| | 1 | 0.353 (Avg) |

*2562-71-1 is a 10 wt. % solution of poly(isobutylene-co-N,N-dimethylvinylbenzylamine) in toluene

**GPI (gas permeability index) is calculated according to the formula:

$$GPI = \frac{P_c}{P_p} \text{ where } P_c = \text{permeability of the nanocomposite and}$$

$P_p$ = the permeability of the polymer.

As can be seen from Table 2, the additional of the poly(isobutylene-co-N,N-dimethylvinylbenzylamine) treated clay to butyl rubber lowers the gas permeability of the butyl rubber.

Example 6

Synthesis of PIBAS

The synthesis starts with polyisobutylene succinic anhydride (PIBSA). PIBSA has been obtained from the Chevron Chemical Company and is made by a thermal process. The PIBSA used is ORONITE® OL15500 with a Mn~1,000 and Mw~1,900. PIBSA is a viscous liquid.

200.9 g. of PIBSA was 25 weighed into a beaker. 25 ml of 3-(dimethylamino)propylamine [M.W.=102.18 g/m, d=0.812] was added and mixed in. An exotherm occurred. The mixture was heated to 150° C., maintained at 150° C. for 5 minutes and then allowed to cool. The resulting material is a medium viscosity oil. This material is designated polyisobutylene succinimide amine (PIBSIA). 40 ml. of 5.2M HCl in $H_2O$ was added and mixed in. The solution was then thickened to a paste. This is PIBAS with occluded water. PIBAS is an acronym for the polyisobutylene amine salt. The amine salt of dimethylaminopropylamine amine may also be present.

Examples 6A

Synthesis of PIBQS 300 g of PIBSA was weighed into a beaker. 15.9 g of dimethylaminopropylamine was added to the PIBSA. The mixture was heated in a boiling water bath for about one hour. 161.4 g of this product was thoroughly mixed with 13.5 g of α,α'dibromoxylene in a beaker and heated in a 90° C. oven for sixteen hours. The product was a PIBQS.

Examples 7-13

Clay Exfoliation

Figure 2:
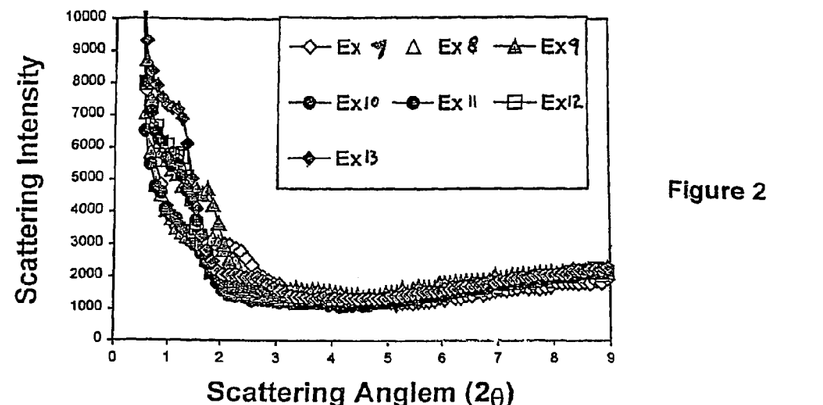
FIG. 2 shows small angle x-ray scattering (SAXS) of PIBQS exfoliated clay in butyl rubber.

Three one-liter bottles were used for the preparations. The amounts and the components are listed in Table 3 below. Toluene, butyl rubber (MH-11) the treated silicate (Example 2), and the PIBAS (Example 6) were charged into the bottle. The bottle was then placed on a mechanical shaker. After about 24 hours, the polymer and the treated silicate were dissolved into the toluene solvent. The solution was then poured into EtOH solvent to extract excess surfactant. The precipitated stock was then drum-dried. The products were checked by using the small angle x-ray scattering (SAXS). The x-ray scattering results showed that adding PIBAS largely improves the exfoliation of the clay into the butyl rubber (FIG. 2). Using a suitable amount of PIBAS, the montmorillonite lamellar x-ray scattering peak in the stock can be shifted to low angle and eventually disappears, which indicates that the clay is finally exfoliated. However, the concentration of PIBAS plays an important role. As can be seen from the scattering chart, if one adds too much PIBAS, another peak at the low angle appears.

TABLE 3

| | Ex 7 | Ex 8 | Ex 9 | Ex 10 | Ex 11 | Ex 12 | Ex 13 |
|---|---|---|---|---|---|---|---|
| Toluene ml | 300 | → | → | → | → | → | → |
| MH-11 (g) | 40 | → | → | → | → | → | → |
| Treated silicate (g) | 4 | → | → | → | → | → | → |
| PIBAS | 0 | 2 | 4 | 6 | 8 | 10 | 12 |

Table 4 shows the effects of PIBAS treated clay on gas permeability of butyl rubber:

TABLE 4

| Pure Butyl Rubber (GPI - gas permeability index) | Butyl Rubber + organo-clay + end/F PIBAS (GPI - gas permeability index) |
|---|---|
| 1 | 0.401 |
| 1 | 0.530 |
| 1 | 0.328 |
| 1 | 0.408 |
| 1 | 0.415 |
| | (Avg) |

As can be seen from Table 4, the addition of PIBAS treated clay to the butyl rubber lowers the gas permeability of the butyl rubber.

The following examples illustrate the dry mixing exfoliation technique according to the present invention:

Example 14

Organo Treated Clay

To a 45 g portion of the PIBAS polymer surfactant produced according to Example 6 was added 100 ml THF and 30 ml alcohol. This mixture was then shaken for 30 minutes at room temperature until the polymer surfactant was dissolved. Separately, 15 g of montmorillonite-clay (Cloisite Na from Southern Clay Products, Gonzales, Tex.) was mixed with 15 ml water. The clay water mixture was allowed to sit at room temperature for about one hour to swell the clay. The swelled clay and the polymer surfactant compositions were then combined and shaken for about twenty-four hours. To give the final product, the clay was then filtered and dried.

Example 15

Exfoliated Clay/Butyl Rubber Via Dry Mixing

Figure 3:
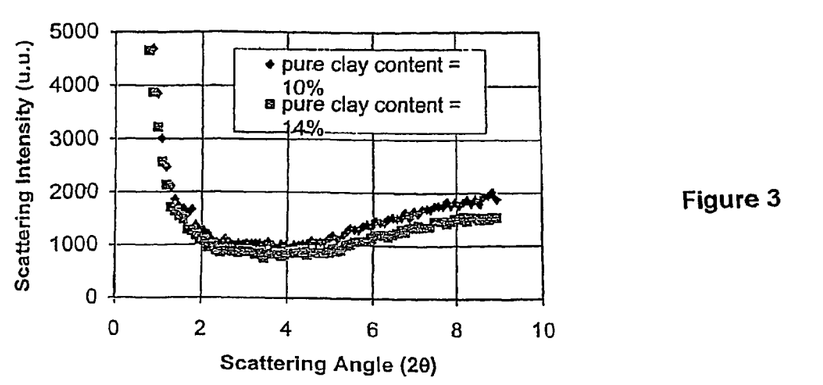
FIG. 3 shows small angle x-ray scattering (SAXS) of PIBQS exfoliated clay which has been dry mixed in butyl rubber.
Figure 4:
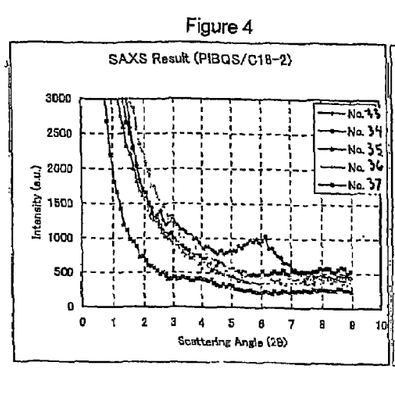
FIG. 4 shows small angle x-ray scattering (SAXS) for PIBQS exfoliated clay with and without low molecular weight surfactant contributions as dry mixed in butyl rubber.
Figure 5:
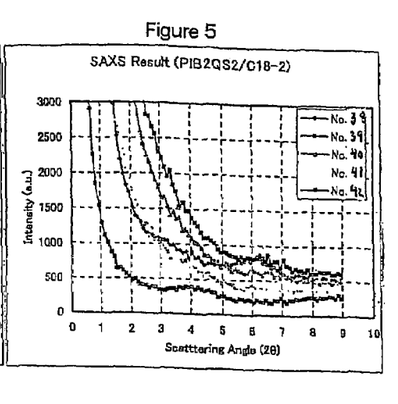
FIG. 5 shows comparative small angle x-ray scattering (SAXS) for $PIB_2QS_2$ exfoliated clay with and without low molecular weight surfactant contributions as dry mixed in butyl rubber.
Figure 6:
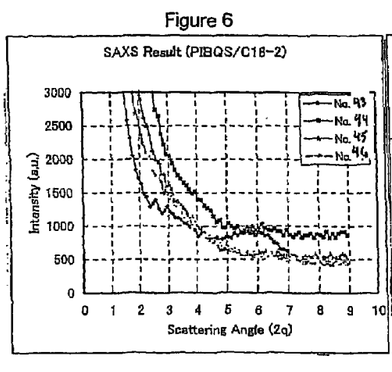
FIG. 6 shows comparative small angle x-ray scattering (SAXS) for PIBQS exfoliated clay with and without low molecular weight surfactant contributions as dry mixed in butyl rubber.
Figure 7:
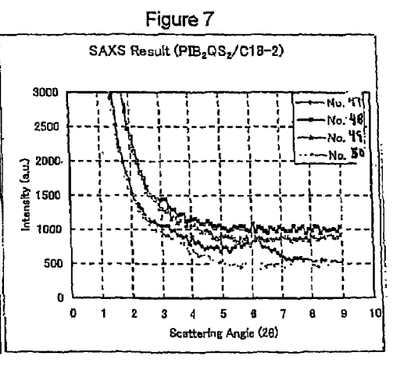
FIG. 7 shows comparative small angle x-ray scattering (SAXS) for $PIB_2QS_2$ exfoliated clay with and without low molecular weight surfactant contributions as dry mixed in butyl rubber.

A 40 g sample of butyl rubber was mixed with 16 g of the organo-clay of Example 13 in a 60 g-Brabender mixer at 70°

C. at 60 rpm for three minutes. Using x-ray scattering, the clay in the rubber compound was determined to be completely exfoliated (see FIG. 3).

The following results in Table 5 show the effect on gas permeability of butyl rubber using PIBAS treated clay produced in accordance with the process described in Example 14.

Permeability Results of Rubber Compounds Containing PIBAS Treated Clay

TABLE 5

|  | 15A | 15B | 15C | 15D |
|---|---|---|---|---|
| Butyl Rubber | 40 | 40 | 35 | 40 |
| PIBAS Treated Clay[1] | 4 | 16 | 23 | 0 |
| Pure Clay (%) | 3% | 10% | 14% | 0% |
| Permeability (GPI) |  |  |  |  |
| Test 1 | 1.042 | 0.672 | 0.596 | 1 |
| Test 2 | 0.899 | 0.616 | 0.534 | 1 |
| Test 3 | 0.931 | 0.659 | 0.571 | 1 |
| Test 4 | 0.858 | 0.650 | 0.600 | 1 |
| Average | 0.926 | 0.648 | 0.576 | 1 |

[1] PIBAS Clay contains 65% PIBQS, as measured by TGA. The data was measured using a MOCON instrument (Mocon, Inc., Minneapolis, Minnesota).

As can be seen from the above test results, rubber compositions containing the newly synthesized PIBAS treated clay (15A-15C) have reduced gas permeability compared to compositions without the treated clay (15D).

Example 16

Organic-Montmorillonite

The layered silicate was a montmorillonite (a natural Bentonite clay from Southern Clay Products, Gonzales, Tex.) with a charge exchange capacity (CEC) of about 98 mequiv/100 g. The clay was organically modified with benzalkoniuim choride (Aldrich, Milwaukee, Wis.) through a cation exchange reaction. In this reaction, 200 mL of a benzalkonium choride/water solution (30 wt %) was used to treat 50 g the clay. The reaction was performed in a sealed flask and the reactants were shaken for 20 hrs at 23° C. The mixture was then filtered through a filter paper. Thereafter, the clay was disposed in another 200 mL of the benzalkonium choride/water solution. The process was repeated three times. Finally, excess benzalkonium choride was removed using isopropanol to wash the product. After vacuum drying, the modified montmorillonite contained about 45% organo-matter (i.e., benzalkonium), as measured by thermo-gravity analysis (TGA). TGA was carried out on equipment manufactured by TA Instruments and Perkin Elmer, among others.

Examples 17-19

Clay Particle Exfoliation

Three 4 L bottles were used for the preparations. The amounts and the components for each example are listed in the Table 6 below. Toluene (Aldrich, Milwaukee, Wis.), Exxpro™ (Exxon, Houston, Tex.) rubber and the organically modified clay from Example 16 were charged into the bottle. The bottle was then placed on a bottle roller at about 30 rpm. After about 48 hrs, the rubber and the treated clay were dissolved in the toluene solvent. The solution was then drum-dried, and the resultant products analyzed via small angle x-ray scattering (SAXS) and transmission electron microscopy (TEM). The x-ray scattering showed no montmorillonite lamellar peak in the materials (i.e. full exfoliation had occurred). A TEM picture showed a montmorillonite plate of about 1,000 nm and an aspect ratio of about 1,000.

TABLE 6

|  | Example 17 | Example 18 | Example 19 |
|---|---|---|---|
| Toluene (g) | 2300 | 2300 | 2300 |
| Exxpro 96-4 (g) | 350 | 350 | 350 |
| Treated clay (g) | 35 | 70 | 105 |

Examples 20-30

Rubber Compounding

Eleven kinds of rubber compositions were prepared according to the formulations shown in Tables 7 and 8 by selectively using the exfoliated clay from Examples 17-19 in compound formulations. In each example, a blend of the ingredients was kneaded by the method listed in Table 9. The final stock was sheeted and molded at 160° C. for 25 minutes. In Examples 20-30, measurement of tensile strength is based on conditions of ASTM-D 412 at 22° C. Test specimen geometry was measured via a ring with a width of 0.05 inches (0.127 cm) and a thickness of 0.075 inches (0.191 cm). Air permeability tests were conducted on 1 mm thick sheets according to ASTM Standard D1434. The physical characteristics of the compositions of Examples 20-30 are shown in Table 10.

TABLE 7

|  | Ex 20 | Ex 21 | Ex 22 | Ex 23 | Ex 24 | Ex 25 | Ex 26 | Ex 27 | Ex 28 | Ex 29 | Ex 30 |
|---|---|---|---|---|---|---|---|---|---|---|---|
| Exxpro ™ 96-4 (g) | 100 |  |  |  |  |  | 50 |  |  |  |  |
| Ex 2 (g) |  | 100 |  |  |  |  |  |  |  |  |  |
| Ex 3 (g) |  |  | 100 |  |  | 50 |  |  |  |  |  |
| Ex 4 (g) |  |  |  | 100 |  |  | 50 |  |  |  |  |
| Butyl Rubber (g) |  |  |  |  | 100 | 50 | 50 | 50 | 95 | 90 | 85 |
| Carbon Black (g) |  |  |  |  |  |  |  |  | 5 | 10 | 15 |
| Naphthenic Oil (g) | 15 | 15 | 15 | 15 | 15 | 15 | 15 | 15 | 15 | 15 | 15 |

TABLE 8

Final Batch Formulation (For Examples 19 to 29, by parts)

| | |
|---|---|
| Stearic acid | 0.50 |
| Sulfur | 0.40 |
| Zinc Oxide | 0.75 |
| (proceeding add) Rylex 3001 | 0.60 |
| Altax-MBTS (accelerator) | 0.80 |

TABLE 9

Mixing Conditions

Mixer: 300 g Brabender      Agitation Speed: 60 rpm

Mater Batch Stage

| | |
|---|---|
| initial Temperature | 100° C. |
| 0 min | charging polymers |
| 0.5 min | charging oil and Carbon Black |
| 5.0 min | drop |

Final Batch Stage

| | |
|---|---|
| Initial Temperature | 75° C. |
| 0 sec | charging master stock |
| 30 sec | charging curing agent and accelerators |
| 75 sec | drop |

TABLE 10

Physical Characteristics of Examples 20-30

| | Ex 20 | Ex 21 | Ex 22 | Ex 23 | Ex 24 | Ex 25 | Ex 26 | Ex 27 | Ex 28 | Ex 29 | Ex 30 |
|---|---|---|---|---|---|---|---|---|---|---|---|
| Exxpro ™ 96-4 (parts) | 100 | 100 | 100 | 100 | | 50 | 50 | 50 | | | |
| Butyl Rubber M-18 (parts) | | | | | 100 | 50 | 50 | 50 | 95 | 90 | 85 |
| Clay (parts) | 0 | 5 | 10 | 15 | 0 | 5 | 7.5 | 0 | | | |
| Carbon Black (parts) | | | | | | | | | 5 | 10 | 15 |
| Tb (kPa) | 1,247 | 3,204 | 5,016 | 6,470 | 1,957 | 4,217 | 4,162 | 1,275 | 2,425 | 3,934 | 5,981 |
| Eb (%) | 369 | 629 | 544 | 418 | 1053 | 782 | 808 | 577 | 1083 | 1010 | 958 |
| Mooney Viscosity @ 300° C. | 135 | 248 | 504 | 716 | 66 | 207 | 206 | 86 | 65 | 82 | 103 |
| Mooney Viscsosisty @ 50° C. | 41 | 73 | 127 | 193 | 33 | 61 | 66 | 36 | 36 | 43 | 48 |
| Air Permeability mL/m²day (66° C.) | 166 | 111 | 99 | 73 | 170 | 132 | 177 | 177 | 164 | 162 | 199 |

Example 31

Synthesis of PIBQS 105.5 g of polyisobutylene succinic anhydride and 5.12 g of 3-(dimethyl amino)propylamine were mixed at room temperature, and then heated to between 95 and 100° C. for 3 hours. To the mixture, 4.1 ml of 12.1N HCl was added and mixed. The mixture was heated between 95 and 100° C. for 3 hours. To remove water, the mixture was kept in a vacuum oven at 100° C. for a day.

Example 32

Synthesis of $PIB_2QS_2$ 400 g of polyisobutylene succinic anhydride and 20.1 g of 3-(dimethyl amino)propylamine. The materials were mixed at room temperature, and then heated between 95 and 100° C. for one hour. To the mixture, 25.9 g of α,α'-ρ-dibromo-xylene was added and mixed. The mixture was heated between 95 and 100° C. for one hour. The mixture was kept in the vacuum oven at 100° C. for 4 hours to remove water.

Example 33-50

Making the Organo-treated Clay

A small amount of the polymer exfoliant of Example 31 or 32, according to Table 11, and 6.7 g THF were combined. The mixture was then shaken for 30 min at room temperature until the polymer exfoliant was dissolved.

1 g of (Cloisite Na) clay and a small amount of dioctadecyldimethyl ammonium (low molecular weight surfactant) according to Table 11 were combined. To the mixture of the clay and the low molecular weight surfactant, the mixture of polymer exfoliant was added, and then shaken for a minute.

2 g of alcohol was added to the mixture and then 1 g water was added. The mixture was shaken for more than 1 day.

To obtain the final product, the mixture was filtered and dried in vacuum.

TABLE 11

| | | Sample No. | | | | | | | | | |
|---|---|---|---|---|---|---|---|---|---|---|---|
| | | 33 | 34 | 35 | 36 | 37 | 38 | 39 | 40 | 41 | 42 |
| Clay (Cloisite Na) (gram) | | 1.00 | 1.00 | 1.00 | 1.00 | 1.00 | 1.00 | 1.00 | 1.00 | 1.00 | 1.00 |
| Polymer surfactant | PIBQS (gram) | 1.00 | 1.00 | 0.70 | 0.40 | 0.10 | 0.00 | 0.00 | 0.00 | 0.00 | 0.00 |
| | PIB$_2$QS$_2$ (gram) | 0.00 | 0.00 | 0.00 | 0.00 | 0.00 | 1.00 | 1.00 | 0.70 | 0.40 | 0.10 |
| Low molecular weight surfactant | C18-2 (gram) | 0.00 | 0.63 | 0.44 | 0.25 | 0.06 | 0.00 | 0.630 | 0.44 | 0.25 | 0.06 |

| | | Sample No. | | | | | | | |
|---|---|---|---|---|---|---|---|---|---|
| | | 43 | 44 | 45 | 46 | 47 | 48 | 49 | 50 |
| Clay (Cloisite Na) | | 1.00 | 1.00 | 1.00 | 1.00 | 1.00 | 1.00 | 1.00 | 1.00 |
| Polymer surfactant | PIBQS (gram) | 1.00 | 1.00 | 0.70 | 0.40 | 0.10 | 0.00 | 0.00 | 0.00 |
| | PIB$_2$QS$_2$ (gram) | 0.00 | 0.00 | 0.00 | 0.00 | 0.00 | 1.00 | 1.00 | 0.70 |
| Low molecular weight surfactant | C18-2 (gram) | 0.00 | 0.63 | 0.44 | 0.25 | 0.06 | 0.00 | 0.630 | 0.44 |

C18-2; dimethyldioctadecylammonium bromide

Thermo-gravity analysis (TGA) showed that the clay contained 41% of the organo-clay. Checked by low molecular weight angle x-ray, the clay was completely exfoliated (see FIGS. 4-7).

The butyl rubber compositions of the present invention can be formulated into any component or article for which butyl rubber is typically utilized. Typical articles for which the butyl rubber compositions can be used include, but are not limited to, inner-tubes and tire inner liners, air cushions, pneumatic sprays, air bags, tire-curing bladders, high temperature hoses and conveyor belts, damping mounts for engines and the like.

The invention has been described with reference to the exemplary embodiments. Modifications and alterations may appear to others upon reading and understanding the specification. The invention is intended to include such modifications and alterations insofar as they come within the scope of the claims.

The invention claimed is:

1. A butyl rubber composition of low gas permeability comprising:
   a) an organically-modified clay,
   b) butyl rubber, and
   c) a polyisobutylene-based exfoliant, in which said organically-modified clay is intercalated by said polyisobutylene-based exfoliant and said butyl rubber;
   wherein the polyisobutylene-based exfoliant is PIBQS, PIB$_2$QS$_2$, or PIBAS.

2. The composition of claim 1 wherein the butyl rubber composition includes between about 10 and 90 wt. % of an organically-modified clay that is capable of being exfoliated.

3. The composition of claim 1 wherein said organically-modified clay is derived from the combination of a low molecular weight surfactant with a clay selected from the group consisting of smectite, pyrophyllite, illites, glauconites, vermiculites, polygorskines, sepiolites, allophanes, imogolites, montmorillonite, synthetic mica and mixtures thereof.

4. The composition of claim 3 wherein said low molecular weight surfactant is selected from the group of organic salts having the general formula:

wherein X is a halide and R1, R2, R3, and R4 are selected from H and $C_1$-$C_{20}$ alkyl chains, which may be linear or branched, further wherein the alkyl chain may optionally contain an aromatic moiety and wherein at least one of the $R^1$-$R^4$ is a $C_4$-$C_{30}$ alkyl chain, which may be linear or branched any may optionally contain a aromatic moiety.

5. The composition of claim 3 wherein said low molecular weight surfactant comprises an organic ammonium salt.

6. A method for lowering the gas permeability of a butyl rubber composition comprising dispersing an exfoliated clay in a butyl rubber compound wherein said exfoliated clay is derived from the reaction of an organically-modified clay and a polymeric exfoliant;
   wherein the polymeric exfoliant is PIBQS, PIB$_2$QS$_2$, or PIBAS.

7. The method of claim 6 wherein said organically modified clay is obtained by combining a clay and organic surfactant having a molecular weight below about 2000.

8. The method of claim 6 wherein said butyl rubber composition comprises between about 10 and 90 wt. % exfoliated clay.

9. The method of claim 6 wherein said butyl rubber comprises one of bromo-butyl rubber, chloro-butyl rubber, butyl extended rubber, or mixtures thereof.

10. A dry mixing process, wherein the dry mixing is done in the substantial absence of solvent, for providing a butyl rubber composition having low gas permeability comprising:
   a) modifying a clay using at least one organic surfactant having a molecular weight below about 2000 to produce an organically modified clay;
   b) exfoliating the organically-modified clay with a polymeric exfoliant selected from the group consisting of polyisobutylene-based exfoliant and modified butyl rubber by admixing the polymeric exfoliant with the organically modified clay to produce an exfoliated clay; and
c) dry mixing the exfoliated clay with butyl rubber;
   wherein the polymeric exfoliant is PIBQS, $PIB_2QS_2$, or PIBAS.

11. The process of claim 10 wherein the dry mixing is done by using a mixer selected from a Brabender mixer, a twin-screw extruder and a kneader at a speed of from about 1 to about 500 rpm.

12. The process of claim 10 wherein the dry mixing takes place at a temperature of from about 25° C. to about 300° C.

13. The process of claim 10 wherein the mixing is done at a speed of about 60 rpm at a temperature of about 70° C.

14. The process of claim 10 wherein the dry mixing is done in the absence of solvent.

15. The process of claim 10 wherein the butyl rubber composition comprises between about 10% and 90% by weight exfoliated organically-modified clay.

16. A process for providing a butyl rubber composition having low gas permeability comprising:
   a) dissolving a polymeric exfoliant in a solvent for the polymeric exfoliant;
   b) swelling clay in a mixture of clay and water;
   c) combining the products of steps a) and b);
   d) drying the product of step c) to obtain an organo-clay;
   e) mixing the product of step d) with butyl rubber at about 70° C. to about 175° C. wherein the butyl rubber produced by the process has the organo-clay incorporated therein thereby imparting low gas permeability properties to the butyl rubber;
   wherein the polymeric exfoliant is PIBQS, $PIB_2QS_2$, or PIBAS.

17. The process of claim 16 wherein the solvent is selected from the group consisting of THF, diethyl ether, and MEK.

18. The process of claim 16 wherein the mixture of step e) is mixed at about 30 to about 120 rpm for about two to about ten minutes.

19. A method for exfoliating clay comprising
   a) combining said clay with an organic exfoliant having a molecular weight less than about 700;
   b) combining a polymeric surfactant having a molecular weight greater than about 1,000 with an organic solvent;
   c) combining the mixtures of steps a and b and introducing water thereto; and
   d) drying the mixture of step c and recovering said exfoliated clay;
wherein the organic exfoliant is PIBQS, $PIB_2QS_2$, or PIBAS.

20. The method of claim 19 wherein said organic surfactant comprising an organic salt.

21. The method of claim 20 wherein said organic salt is dioctadecyldimethyl ammonium salt.

* * * * *

UNITED STATES PATENT AND TRADEMARK OFFICE
CERTIFICATE OF CORRECTION

PATENT NO. : 7,576,155 B2 Page 1 of 1
APPLICATION NO. : 10/536278
DATED : August 18, 2009
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 826 days.

Signed and Sealed this

Seventh Day of September, 2010

David J. Kappos
*Director of the United States Patent and Trademark Office*